(12) United States Patent
Geiger

(10) Patent No.: US 10,456,126 B2
(45) Date of Patent: Oct. 29, 2019

(54) FORCEPS WITH INTEGRATED BLADE

(71) Applicant: Chris Geiger, Castle Rock, CO (US)

(72) Inventor: Chris Geiger, Castle Rock, CO (US)

( * ) Notice: Subject to any disclaimer, the term of this patent is extended or adjusted under 35 U.S.C. 154(b) by 551 days.

(21) Appl. No.: 14/875,125

(22) Filed: Oct. 5, 2015

(65) Prior Publication Data

US 2017/0095248 A1 Apr. 6, 2017

(51) Int. Cl.
*A61B 17/04* (2006.01)
*A61B 17/28* (2006.01)

(52) U.S. Cl.
CPC .......... *A61B 17/0467* (2013.01); *A61B 17/28* (2013.01)

(58) Field of Classification Search
CPC ..... A61B 17/28; A61B 17/0467; A61B 17/30; A61B 17/285; A61B 17/0483
See application file for complete search history.

(56) References Cited

U.S. PATENT DOCUMENTS

| | | | |
|---|---|---|---|
| 4,053,979 A * | 10/1977 | Tuthill | A61B 17/0467 30/124 |
| 4,669,470 A | 6/1987 | Brandfield | |
| 4,848,341 A | 7/1989 | Ahmad | |
| 5,015,252 A | 5/1991 | Jones | |
| 2006/0260135 A1* | 11/2006 | Khan-Sullman | A61B 17/0467 30/134 |
| 2007/0251100 A1* | 11/2007 | Fisk | D05B 89/00 30/253 |

FOREIGN PATENT DOCUMENTS

GB 2417919 A 3/2006

* cited by examiner

*Primary Examiner* — Anh T Dang
(74) *Attorney, Agent, or Firm* — Merchant & Gould P.C.

(57) ABSTRACT

An apparatus includes a gripping instrument that includes a first arm and a second arm disposed opposite the first arm. The first arm and the second arm are joined at a joint, where an end of the first arm opposite the joint is configured to move towards an end of the second arm opposite the joint in a gripping direction. The apparatus further includes a blade disposed on the first arm, where the blade is oriented at an angle that is non-parallel to the gripping direction.

17 Claims, 7 Drawing Sheets

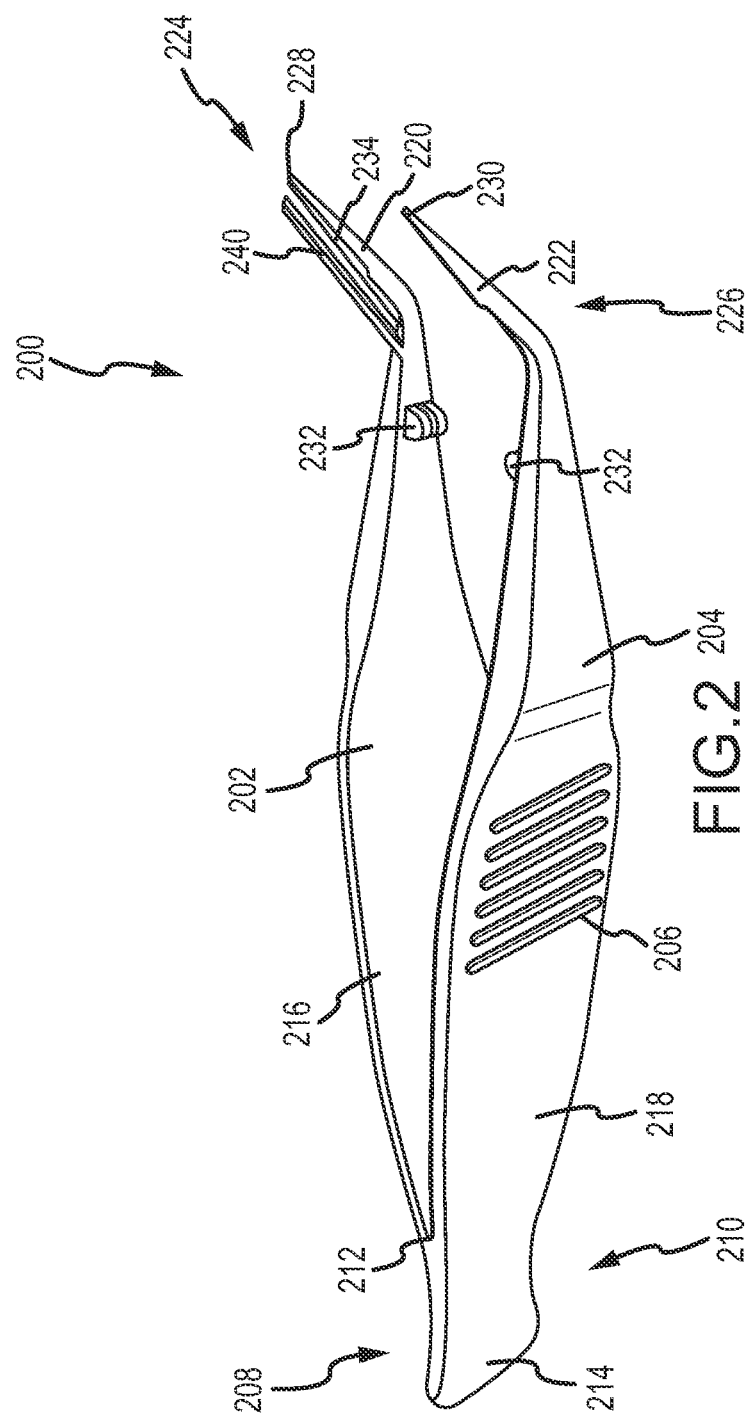

FORCEPS WITH INTEGRATED BLADE

INTRODUCTION

Forceps, tweezers, tongs, and the like are used in medical, hobby, utility, and other applications to aid in gripping and pulling objects, particularly small structures. For example, forceps can be used in medical procedures to aid in the attachment or removal of sutures, for example. After suture attachment, instruments such as scissors are then used to cut the suture to the proper length. A similar procedure is used in suture removal, where the suture is first cut by a pair of scissors, then pulled with a pair of forceps. Both of these procedures require the use of two instruments, either simultaneously in two hands or sequentially in a single hand.

SUMMARY

In one aspect, the technology relates to an apparatus including two arms, where each of the two arms includes a first end and a second end. The two arms are joined at the first ends so as to form a handle. The second ends configured to be positioned in an open position when the two second ends are not in contact and in a closed position where the two second ends are in contact, and when in the open position, the two second ends define two points on a line. The apparatus further includes a blade disposed on at least one of the two arms, with the blade including a body that defines a plane and a cutting edge disposed at an angle to the plane, and where the plane is disposed at an angle to the line.

In another aspect, the technology relates to an apparatus including a gripping instrument that includes a first arm and a second arm disposed opposite the first arm. The first arm and the second arm are joined at a joint, where an end of the first arm opposite the joint is configured to move towards an end of the second arm opposite the joint in a gripping direction. The apparatus further includes a blade disposed on the first arm, where the blade is oriented in at an angle that is non-parallel to the gripping direction.

In another aspect, the technology relates to a method including gripping a gripping instrument in a first orientation and actuating the gripping instrument into a gripping position without releasing the gripping instrument from the first orientation. The method further includes cutting a target with a blade disposed on the gripping instrument, where the cutting operation is performed discrete from the actuating operation and without releasing the gripping instrument from the first orientation.

BRIEF DESCRIPTION OF THE DRAWINGS

There are shown in the drawings, examples which are presently preferred, it being understood, however, that the technology is not limited to the precise arrangements and instrumentalities shown.

FIGS. 2-4 are other examples of gripping instruments with integral cutting blades.

DETAILED DESCRIPTION

In general, forceps, tweezers, tongs, or other gripping instruments have a pair of arms that are used to grip an object, usually by application of a squeezing force on the instrument (depending on instrument configuration). Certain of these instruments may also be locked in one or more positions. When in an open position, the arms of the instrument are spread away from each other, in examples by a spring or return force inherent in the material used to manufacture the instrument. Other types of instruments (e.g., forceps such as Pean, Gross-Maier, etc.) include a pivoting connection joining the two arms. Thumb and finger holes at the ends of these arms allow the gripping ends of the arms to be moved further apart and closer together. In the case of instruments having a pivoting connection, the thumb and finger holes allow those instruments to operate much like a pair of scissors. However, when the arms of such instruments are brought into a gripping position (with the tips close together, usually with an object present therebetween), the gripping portions merely grip the object without cutting or slicing as is the case with scissors.

The integrated blade technologies described herein dispose one or more blades on one or more arms of the instrument in such a configuration that gripping objects is still possible, as with regular forceps. However, the configuration (e.g., orientation, angle, size, length, etc.) of the blade prevents the blade from cutting the object as the arms are brought into the gripping position. That is, the blade is not oriented so as to face the opposite arm, which would result in the blade cutting the target (again, much like scissors). This enables a user of the instrument to use the forceps in a typical manner, while still having in hand and readily available, a slicing blade to allow for easy cutting of a target, if desired.

As such, a user may utilize both functions of the blade-integrated forceps, without having to trade instruments, or utilize a cutting implement disposed, e.g., on an end of the instrument opposite the gripping portion. The integrated blade technologies described herein may be applied to forceps, tweezers, tongs, or other gripping instruments that are used to enable or supplement the gripping of objects, especially very fine or small objects. For clarity herein, however, the technologies will be described generally in the context of medical forceps used for the insertion and removal of sutures.

Figure 1A:
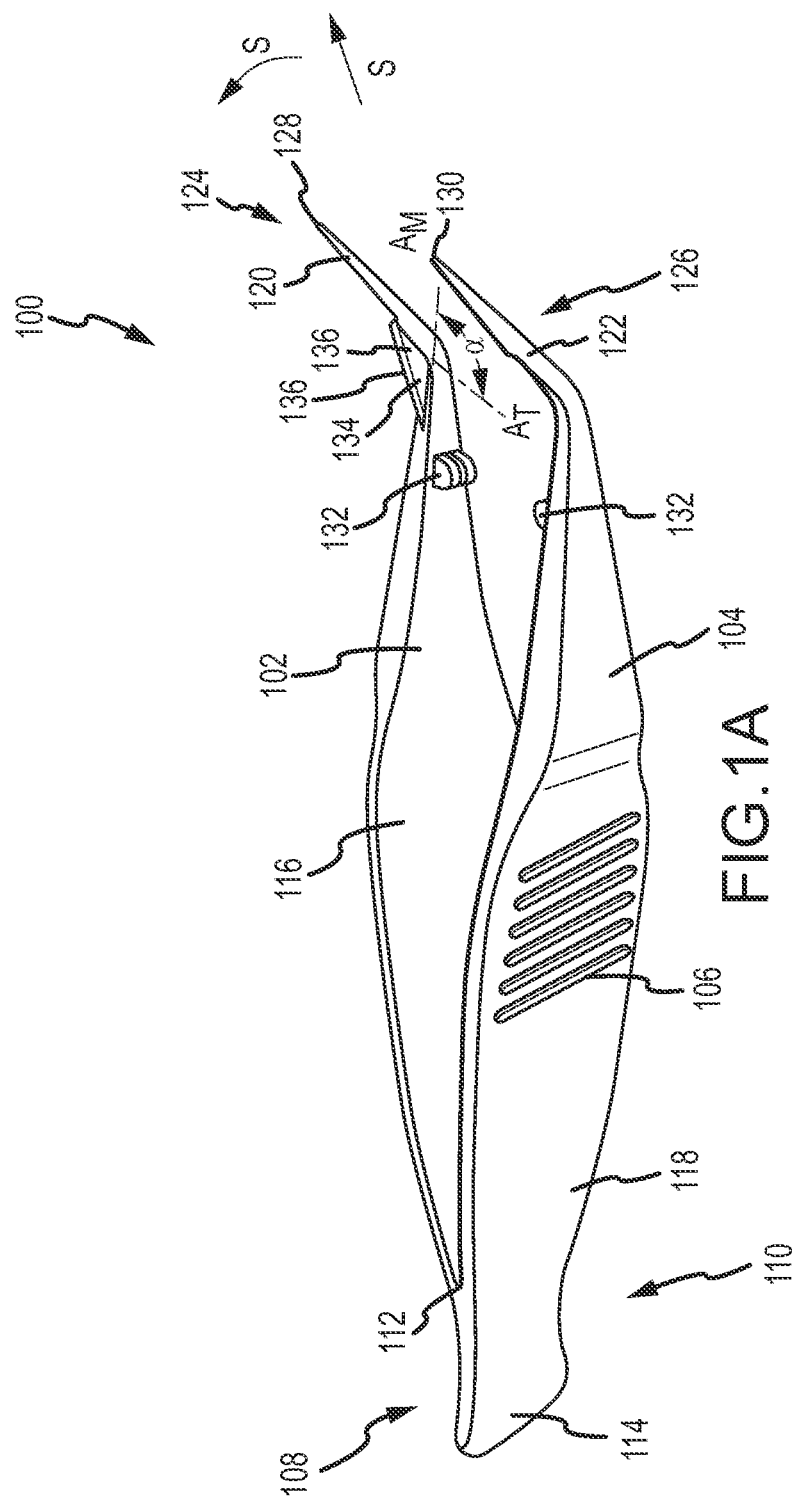
FIGS. 1A and 1B depict perspective and end views, respectively, of a gripping instrument with integral cutting blades.
Figure 1B:
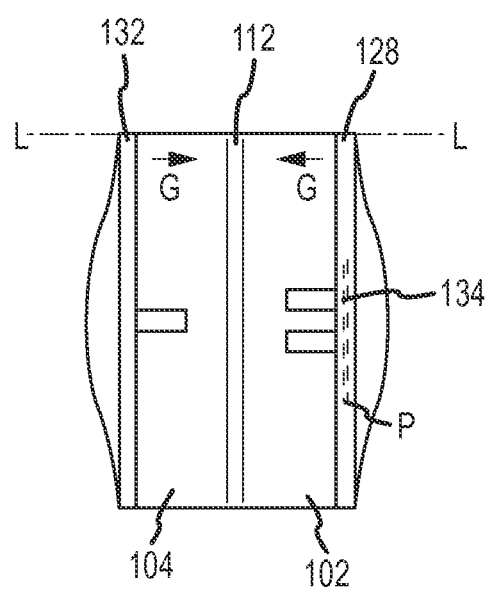

FIG. 1A is a perspective view of a gripping instrument, in this case, a pair of forceps 100. FIG. 1B is an end view of the forceps 100 and is described simultaneously with FIG. 1A. The forceps 100 include two arms 102, 104, each including on an exterior thereof one or more raised serrations, ribs, or ridges 106 to improve gripping of the forceps 100. The arms 102, 104 are connected at first ends 108, 110 thereof to form a joint 112 so as to form a handle 114. Typically, during use, the handle 114 of the forceps 100 may rest in or be cupped by the palm of the hand, while one finger and the thumb may apply opposing forces to the arms 102, 104 (whether the thumb or finger applies force to arm 102 or arm 104 is a function of how, and in which hand, the forceps 100 are held).

The arms 102, 104 each include a main portion 116, 118 (typically where the forceps 100 are gripped by a user) and a tip portion 120, 122 (typically where the forceps 100 capture an object). Second ends 124, 126 of each arm 102, 104 are located distal from the handle 114 and each include a tip 128, 130. In general, the tips 128, 130 may be the distal ends of the tip portions 120, 122 that contact each other when the two arms 102, 104 are forced together (without an object therebetween). Textured surfaces may be disposed thereon to reduce slipping of the object being gripped. Stops 132 may prevent over-squeezing and potentially bending of the arms 102, 104 when the tips 128, 130 are in contact.

At least one blade 134 is disposed on the forceps 100, more specifically, on arm 102. The blade 134 may be disposed in a number of locations, but in the depicted example, the blade 134 spans, and is connected to, both the main portion 116 and the tip portion 120 of the arm 102. More specifically, the main portion 116 includes a main axis $A_M$, while the tip portion 120 includes a tip axis $A_T$. These axes $A_M$, $A_T$ are disposed at an angle α to each other, and the blade 134 spans that angle α. The blade 134 includes a body 136 and a cutting edge 138 disposed at an angle to the body 136, as typical of common blades.

FIG. 1B is an end view of the gripping instrument 100 of FIG. 1B and depicts the instrument 100, viewed from the tips 128, 130, towards the handle 114. In FIG. 1A, the instrument (again, forceps) 100 are in an open position. Each arm 102, 104 terminates at the tips 128, 130. When the forceps 100 are squeezed, the tips 128, 130 move towards each other in a gripping direction G, until they reach a closed position where they touch (or until they grip an object therebetween). The tips 128, 130 also define two points on a line L therebetween. The gripping direction G is generally along this line L. The blade 134 forms a plane P (depicted here as a two-dimensional line). This plane P is disposed at an angle β to the line L. The angle β may be any angle that reduces or minimizes the likelihood that the blade 134 will cut an object when the object is being gripped. In examples, this angle β is generally non-parallel to the line L or the gripping direction G. One potential orientation utilized so as to avoid cutting of an object is when the plane P is substantially orthogonal to the line L. In other examples, the angle β is between about 90 degrees and about 75 degrees to the line L or the gripping direction G. In a contrary example, common scissors include blades on the arms that are generally disposed parallel to a closing direction (which is substantially similar to the gripping direction G of the instrument 100). As such, this orientation enables cutting when arms of the scissors are brought together. The non-parallel orientation of the blade 134 on the gripping instrument 100 prevents cutting of an object as the arms 102, 104 are brought together.

With the depicted orientation of the blade 134, the instrument 100 may be used for both gripping and cutting operations. For example, the instrument is typically held in a first orientation, where the thumb is in contact with a first arm 102, while the index finger is in contact with the second arm 104. A user, e.g., a surgeon, may actuate the gripping action of the instrument to grip G and pull sutures being used to close a wound. At the end of the suturing operation, the blade 134 may be used to simply slice the suture to the proper length, without using the gripping function of the instrument 100, and without changing the first orientation of the instrument 100. The slicing action S can be performed, e.g., by lifting the tip 128 of the instrument 100 (from below the suture) or by moving the tip 128 forward in a substantially linear motion. As such, the instrument 100 with integral blade 134 is much easier to use than instruments that incorporate cutting implements on an end opposite the gripping portion.

Figure 3:
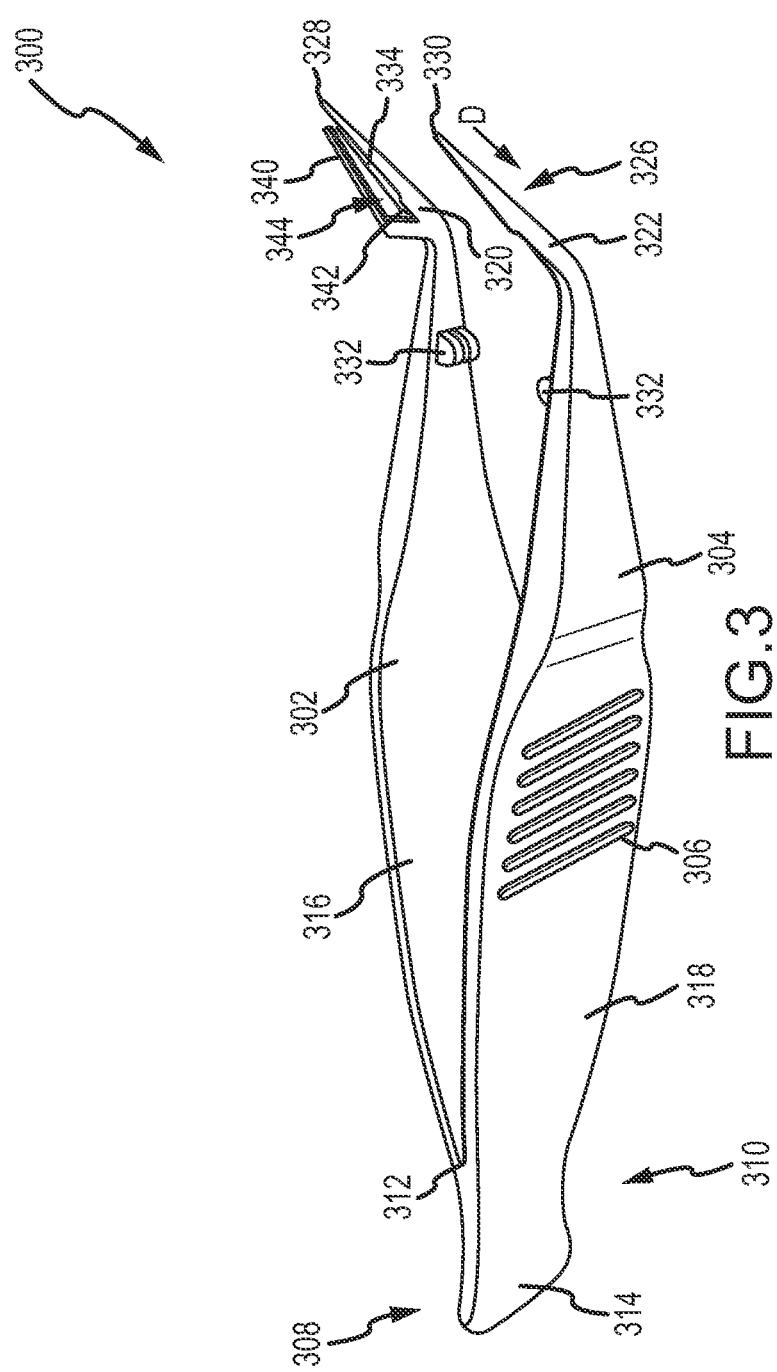
Figure 4:
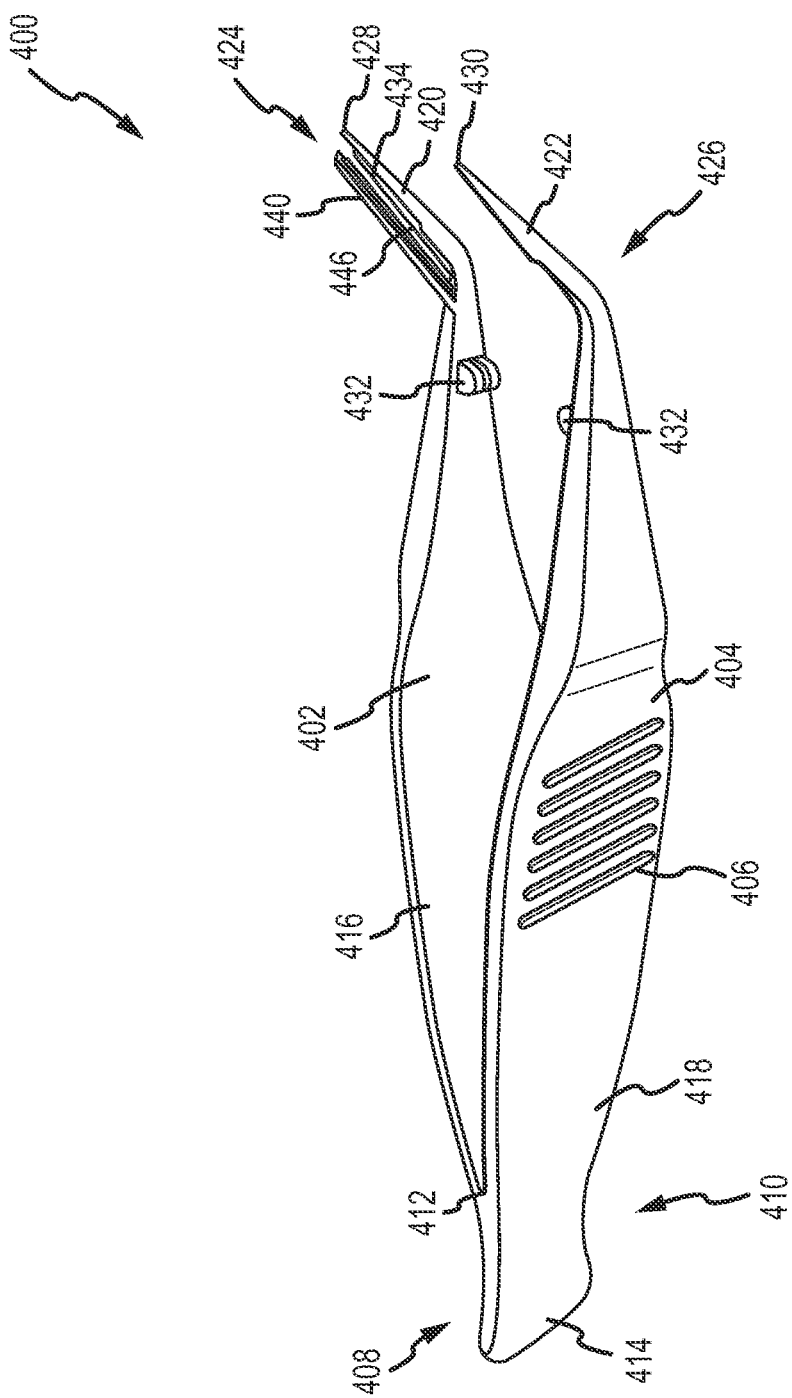

FIGS. 2-4 are other examples of gripping instruments 200, 300, 400 with integrated cutting blades. The gripping instruments 200, 300, 400 of FIGS. 2-4 include structures and components similar to those depicted and described in FIGS. 1A and 1B, which are similarly numbered. As such, certain of these elements are not described further. The orientations, configurations, and other details of cutting blades 234, 334, 434 are described further with regard to FIGS. 2-4.

In FIG. 2, the gripping instrument 200 includes a guard 240 that extends from a main portion 216 of the first arm 202. A blade 234 is configured so as to project from and be connected to the tip portion 220. An end of the blade 234 may be secured to the main portion 216 so as to further stabilize the blade 234, if required or desired. The blade 234 may be secured to the tip portion 220 so as to be substantially parallel, or at a slight angle, thereto. The guard 240 is substantially parallel to the tip portion 220 and is disposed so as to be aligned with the tip portion 220. As such, the blade 234 is disposed between the guard 240 and the tip portion 220, and substantially parallel to both.

In FIG. 3, the gripping instrument 300 includes a guard 340 that extends from a tip portion 320 of the first arm 302. A blade 334 is configured so as to project from and be connected to the tip portion 320. The blade 334 may be secured to the tip portion 320 so as to be substantially parallel, or at a slight angle, thereto. The guard 340 is substantially parallel to the tip portion 120 and is disposed so as to be aligned with the tip portion 320. As such, the blade 334 is disposed between the guard 340 and the tip portion 320, and substantially parallel to both. The blade 334 may include two cutting edges. A first, longer cutting edge 138 is disposed so as to be substantially parallel to the guard 340. A second cutting edge 342 may be disposed at an end of the blade 334. As such, a gap 344 may be formed between the guard 340 and the second cutting edge 342. The instrument 300 may be manipulated by a user such that a loop or length of material (e.g., a suture) is disposed in the gap 344, then the instrument 100 may be moved in a direction D, so the material is brought into contact with the second cutting edge 342 and cut.

In FIG. 4, the gripping instrument 400 includes a guard 440 that extends from a main portion 416 of the first arm 402. A first blade 434 is configured so as to project from and be connected to the tip portion 420. An end of the blade 434 may be secured to the main portion 416 so as to further stabilize the blade 434, if required or desired. The blade 434 may be secured to the tip portion 420 so as to be substantially parallel, or at a slight angle, thereto. The guard 440 is substantially parallel to the tip portion 420 and is disposed so as to be substantially aligned with the tip portion 420. As such, the blade 434 is disposed between the guard 440 and the tip portion 420, and substantially parallel to both. This instrument 400 includes a second blade 446 extending from the guard 440 and facing substantially towards the first blade 434. This second blade 446 can also be used for cutting, by manipulating the instrument in a downward direction D, or a slicing direction S.

Figure 5:
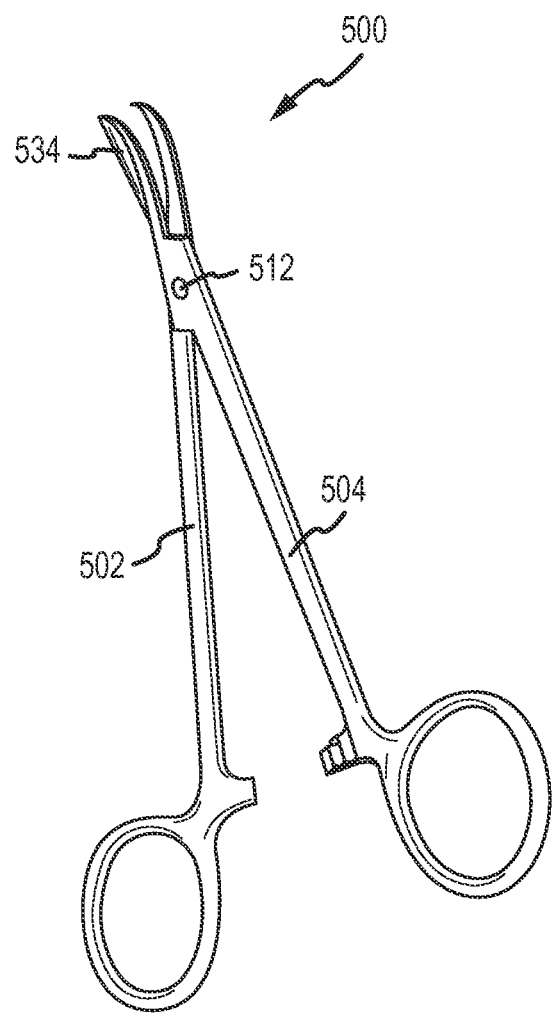
FIGS. 5-6 are other examples of gripping instruments with integral cutting blades.
Figure 6:
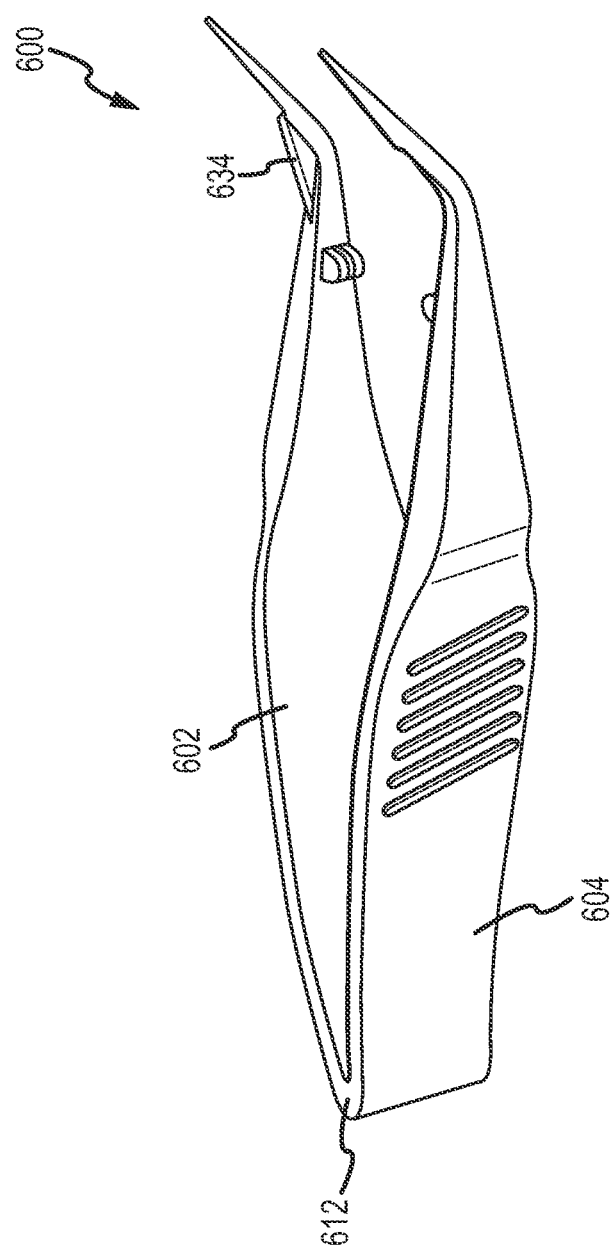

In the embodiments depicted above in FIGS. 1-4, the gripping instruments have one or more blades attached thereto. As noted, these gripping instruments include two arms joined via a weld or adhesive at the joint. The incorporation of blades into other types of gripping instruments is also contemplated, however. For example, FIG. 5 depicts a gripping instrument 500 having two arms 502, 504 joined at a joint 512. The joint 512 is, in this case, a pivoting connection such as a rivet, screw, or a bolt. As with the other examples depicted herein, a blade 534 can be integrated into one or more of the arms 502, 504, and utilized similarly to the examples described above. FIG. 6 depicts a gripping instrument 600 having two arms 602, 604 joined at a joint 612 that in this case, is a live hinge. As with the other examples depicted herein, a blade 634 can be integrated into one or more of the arms 602, 604, and utilized similarly to the examples described above.

The materials utilized in the manufacture of the instrument may be those typically utilized for other equipment utilized in surgical suites. For instruments that may be reused, metals such as steel, aluminum, or stainless steel can be used. Additionally, robust reinforced plastics can also be used. Such materials utilized in reusable instruments should be able to withstand temperatures generated in an autoclave. Disposable plastics can also be utilized. It may be desirable, however that these materials could also be sterilized prior to use.

The terms first and second, as used herein, are relative terms used for convenience of the reader and to differentiate various elements of the instruments from each other. In general, unless otherwise noted, the terms are not meant to define or otherwise restrict location of any particular element.

While there have been described herein what are to be considered exemplary and preferred examples of the present technology, other modifications of the technology will become apparent to those skilled in the art from the teachings herein. The particular methods of manufacture and geometries disclosed herein are exemplary in nature and are not to be considered limiting. It is therefore desired to be secured in the appended claims all such modifications as fall within the spirit and scope of the technology. Accordingly, what is desired to be secured by Letters Patent is the technology as defined and differentiated in the following claims, and all equivalents.

What is claimed is:

1. An apparatus comprising:
    two arms, each of the two arms including a first end and a second end, wherein the two arms are joined at the first ends so as to form a handle, wherein the second ends are configured to be positioned in an open position where the two second ends are not in contact and in a closed position where the two second ends are in contact, wherein when in the open position, the two second ends define two points on a line, wherein the line defines a gripping direction between the open position and the closed position, wherein at least one of the two arms defines a main portion and a tip portion, wherein the second end of the at least one of the two arms is disposed at a distal end of the tip portion, wherein the main portion extends along a main axis and the tip portion extends along a tip axis, and wherein the tip axis is disposed at a first angle to the main axis; and
    a blade disposed on at least one of the two arms, wherein the blade comprises a body that defines a plane and a cutting edge disposed at a second angle to the plane, wherein the plane is disposed at a third angle that is non-parallel to the line, and wherein the blade spans the first angle between the main portion and the tip portion.

2. The apparatus of claim 1, wherein the blade is connected to the tip portion.

3. The apparatus of claim 2, where the blade is connected to the main portion.

4. The apparatus of claim 1, further comprising a guard connected to the at least one of the two arms, such that the blade is disposed between the tip portion and the guard.

5. The apparatus of claim 4, wherein the guard is connected to the tip portion.

6. The apparatus of claim 4, wherein the guard is connected to the main portion.

7. The apparatus of claim 4, further comprising a guard blade disposed on the guard, wherein the guard blade projects toward the blade.

8. An apparatus comprising:
    a gripping instrument, the gripping instrument comprising a first arm and a second arm disposed opposite the first arm, wherein the first arm and the second arm are joined at a joint, wherein a first end of the first arm opposite the joint is configured to move towards a second end of the second arm opposite the joint in a gripping direction, wherein at least the first arm defines a main portion and a tip portion, wherein the main portion extends along a main axis and the tip portion extends along a tip axis, wherein the tip axis is disposed at a first angle to the main axis, and wherein the first end of the first arm is disposed at a distal end of the tip portion;
    a blade disposed on the tip portion of the first arm, wherein the blade is oriented in at a second angle that is substantially parallel to the tip portion and non-parallel to the gripping direction; and
    a guard disposed on the first arm at a third angle substantially parallel to the tip portion, wherein an edge of the blade is disposed between the guard and the tip portion.

9. The apparatus of claim 8, wherein the second angle is substantially orthogonal to the gripping direction.

10. The apparatus of claim 8, wherein the second angle is between about 90 degrees and about 75 degrees to the gripping direction.

11. The apparatus of claim 8, wherein the gripping instrument is at least one of forceps, tweezers, and tongs.

12. The apparatus of claim 8, wherein the joint comprises at least one of a rivet, a screw, and a bolt.

13. The apparatus of claim 8, wherein the joint comprises a live hinge connecting the first arm and the second arm.

14. The apparatus of claim 8, wherein the joint comprises at least one of an adhesive and a weld.

15. The apparatus of claim 8, further comprising a guard blade disposed on the guard.

16. The apparatus of claim 8, further comprising a blade disposed on the second arm.

17. A method comprising:
    gripping a gripping instrument in a first orientation;
    actuating the gripping instrument into a gripping position without releasing the gripping instrument from the first orientation, wherein the gripping instrument comprises a first arm having a first end and a second arm having a second end, wherein at least the first end is disposed at an angle with respect to an axis of the first arm, and wherein actuating the gripping instrument moves the first end toward the second end in a gripping direction; and
    cutting a target with a blade disposed on the first end of the gripping instrument, wherein the cutting operation is performed discrete from the actuating operation and without releasing the gripping instrument from the first orientation, and wherein the cutting operation is performed at an angle that is non-parallel to the gripping direction.

* * * * *